US00PP22299P2

(12) United States Plant Patent
Brown

(10) Patent No.: US PP22,299 P2
(45) Date of Patent: Dec. 6, 2011

(54) ***MANDEVILLA* PLANT NAMED 'VOG 051'**

(50) Latin Name: *Mandevilla hybrida*
Varietal Denomination: VOG 051

(75) Inventor: Graham Noel Brown, Pennant Hills (AU)

(73) Assignees: Floraquest Pty. Ltd., Pennant Hills, NSW (AU); Protected Plant Promotions Australia Pty. Ltd., Macquarie Fields NSW (AU)

( * ) Notice: Subject to any disclaimer, the term of this patent is extended or adjusted under 35 U.S.C. 154(b) by 1 day.

(21) Appl. No.: 12/799,440

(22) Filed: Apr. 23, 2010

(51) Int. Cl.
*A01H 5/00* (2006.01)

(52) U.S. Cl. ..... Plt./232

(58) Field of Classification Search ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'VOG 051', characterized by its compact, upright and mounding plant habit; strong stems; freely flowering habit; and dark greyed purple-colored flowers.

1 Drawing Sheet

Botanical designation: *Mandevilla hybrida.*
Cultivar denomination: 'VOG 051'.

BACKGROUND OF THE INVENTION

The present invention relates to a new and distinct cultivar of *Mandevilla* plant, botanically known as *Mandevilla hybrida* and hereinafter referred to by the name 'VOG 051'.

The new *Mandevilla* plant is a product of a planned breeding program conducted by the Inventor in Pennant Hills, New South Wales, Australia. The objective of the breeding program is to create new compact shrub-type *Mandevilla* plants with strong stems and numerous attractive flowers.

The new *Mandevilla* plant originated from a cross-pollination made by the Inventor in Pennant Hills, New South Wales, Australia in December, 2003, of a proprietary selection of *Mandevilla hybrida* identified as code number X02.5, not patented, as the female, or seed parent with *Mandevilla hybrida* 'Sunmandecrim', disclosed in U.S. Plant Pat. No. 15,539, as the male, or pollen, parent. The new *Mandevilla* was discovered and selected by the Inventor as a single flowering plant from within the progeny of the stated cross-pollination in a controlled greenhouse environment in Macquarie Fields, New South Wales, Australia in November, 2005.

Asexual reproduction of the new *Mandevilla* plant by cuttings in Macquarie Fields, New South Wales, Australia, since December, 2005, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in cultural practices and environment such as temperature and light intensity without, however, any variance in genotype.

The following traits have been repeatedly observed and are determined to be the unique characteristics of 'VOG 051'. These characteristics in combination distinguish 'VOG 051' as a new and distinct *Mandevilla* plant:

1. Compact, upright and mounding plant habit.
2. Strong stems.

3. Freely flowering habit.
4. Dark greyed purple-colored flowers.

Plants of the new *Mandevilla* can be compared to plants of the female parent selection. Plants of the new *Mandevilla* differ from plants of the female parent selection in the following characteristics:

1. Plants of the new *Mandevilla* have smaller flowers than plants of the female parent selection.
2. Plants of the new *Mandevilla* and the female parent selection differ in flower color as plants of the female parent selection have red-colored flowers.

Plants of the new *Mandevilla* can be compared to plants of the male parent, 'Sunmandecrim'. Plants of the new *Mandevilla* differ from plants of 'Sunmandecrim' in the following characteristics:

1. Plants of the new *Mandevilla* are more compact than plants of 'Sunmandecrim'.
2. Plants of the new *Mandevilla* have thicker stems than plants of 'Sumnandecrim'.
3. Plants of the new *Mandevilla* and 'Sunmandecrim' differ in flower color as plants of 'Sunmandecrim' have crimson red-colored flowers.

Plants of the new *Mandevilla* can also be compared to plants of *Mandevilla hybrida* 'VOG 053', disclosed in U.S. Plant Pat. No. 20,919. Plants of the new *Mandevilla* differ primarily from plants of 'VOG 053' in flower color as plants of 'VOG 053' have dark red-colored flowers.

BRIEF DESCRIPTION OF THE PHOTOGRAPHS

The accompanying colored photographs illustrate the overall appearance of the new *Mandevilla* plant, showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the bottom of the sheet comprises a side perspective view of a typical flowering plant of 'VOG 051' grown in a container.

The photograph at the top of the sheet is a close-up view of a typical open flower and a flower bud of 'VOG 051'.

DETAILED BOTANICAL DESCRIPTION

The aforementioned photographs and following observations, measurements and values describe plants grown in one-gallon containers during the late summer and autumn in a polyethylene-covered greenhouse in Bonsall, Calif. under commercial production cultural practices. During the production of the plants, day temperatures averaged 29.4° C., night temperatures averaged 21.1° C. and light levels ranged from 6,000 to 7,000 foot-candles. Plants were pinched three times and were 10 months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'VOG 051'.

Parentage:

*Female, or seed, parent.*—Proprietary selection of *Mandevilla hybrida* identified as code number X02.5, not patented.

*Male, or pollen, parent.*—*Mandevilla hybrida* 'Sunmandecrim', disclosed in U.S. Plant Pat. No. 15,539.

Propagation:

*Type.*—By cuttings.

*Time to produce a rooted young plant.*—About one month.

*Root description.*—Fleshy, thick; white in color.

*Rooting habit.*—Moderate branching; moderately dense.

Plant description:

*Plant and growth habit.*—Compact, upright and mounding plant habit; vining; vigorous growth habit.

*Plant height.*—About 40 cm.

*Plant diameter.*—About 38 cm by 42 cm.

*Lateral branch description.*—Branching habit: Freely branching habit with about eight primary lateral branches per plant; primary laterals with secondary laterals; pinching enhances lateral branch development. Length: About 34 cm. Diameter: About 5 mm. Internode length: About 2.1 cm. Strength: Strong. Texture: Smooth, glabrous; woody with development. Color, young: Close to 144B. Color, woody: Close to 199A.

Foliage description:

*Arrangement.*—Opposite, simple.

*Length.*—About 5.8 cm.

*Width.*—About 3.3 cm.

*Shape.*—Elliptical.

*Apex.*—Acuminate.

*Base.*—Obtuse.

*Margin.*—Entire.

*Texture, upper and lower surfaces.*—Smooth, glabrous; leathery.

*Venation pattern.*—Pinnate, arcuate.

*Color.*—Developing leaves, upper surface: Close to N137A. Developing leaves, lower surface: Close to 146A. Fully expanded leaves, upper surface: Darker than 147A; venation, close to 147B. Fully expanded leaves, lower surface: Close to 147B; venation, close to 146D.

*Petioles.*—Length: About 1.2 cm. Diameter: About 2 mm. Texture, upper and lower surfaces: Smooth, glabrous. Color, upper surface: Close to 146B. Color, lower surface: Close to 146D.

Flower description:

*Flower type and habit.*—Salverform flowers arranged in loose and open racemes; racemes terminal and axillary; flowers face upright or outwardly; freely flowering habit, about four flowers per raceme and about twelve open flowers and flower buds per lateral branch.

*Natural flowering season.*—Plants flower continuously year-round in the greenhouse and outdoors in Southern California.

*Flower longevity on the plant.*—About five to seven days; flowers not persistent.

*Fragrance.*—None detected.

*Inflorescence height.*—About 9 cm.

*Inflorescence diameter.*—About 8.5 cm.

*Flowers.*—Appearance: Flared trumpet, corolla fused, five-parted; petals imbricate; petal apices reflexed; flowers roughly star-shaped. Diameter: About 6.8 cm. Depth (length): About 6.5 cm.

*Flower buds.*—Height: About 7.8 cm. Diameter: About 1.8 cm. Shape: Elongated oblong. Color: Close to 187B to 187C.

*Corolla.*—Arrangement/appearance: Single whorl of five petals, fused into flared trumpet; petals imbricate with reflexed apices. Petal lobe length: About 3.5 cm. Petal lobe width: About 3 cm. Petal shape: Roughly elliptical. Petal apex: Acuminate, reflexing. Petal margin: Entire. Petal texture, upper and lower surfaces: Smooth, glabrous; velvety. Color: Petal lobe, when opening, upper surface: Close to 187A. Petal lobe, when opening, lower surface: Close to 187B. Petal lobe, fully opened, upper surface: Close to 187A; with development, color towards the throat becomes closer to 183A. Petal lobe, fully opened, lower surface: Close to 187A. Tube: Towards the apex, close to 187B and towards the base, close to 145B. Throat: Close to 175C.

*Sepals.*—Arrangement/appearance: Five per flower fused in a single whorl. Length: About 9 mm. Width: About 2 mm. Shape: Lanceolate. Apex: Acute. Margin: Entire. Texture, upper and lower surfaces: Smooth, glabrous. Color, upper surface: Close to 145C. Color, lower surface: Close to 145B.

*Peduncles.*—Length: About 3.4 cm. Diameter: About 2 mm. Texture: Smooth, glabrous. Strength: Flexible, but strong. Aspect: Upright to about 20° from vertical. Color: Close to 145B.

*Pedicels.*—Length: About 1.7 cm. Diameter: About 2 mm. Texture: Smooth, glabrous. Strength: Flexible, but strong. Aspect: About 30° to 45° from peduncle axis. Color: Close to 146D.

*Reproductive organs.*—Stamens: Quantity per flower: Typically five. Filament length: About 2 mm. Filament color: Close to 150D. Anther shape: Lanceolate. Anther length: About 9 mm. Anther color: Close to 158A. Pollen amount: Scarce. Pollen color: Close to 158A. Pistils: Quantity per flower: Typically one. Pistil length: About 2.8 cm. Stigma shape: Rounded. Stigma color: Close to 144C. Style length: About 2 cm. Style color: Close to 150C. Ovary color: Close to 144A.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 2° C. to about 35° C.

It is claimed:

1. A new and distinct *Mandevilla* plant named 'VOG 051' as illustrated and described.

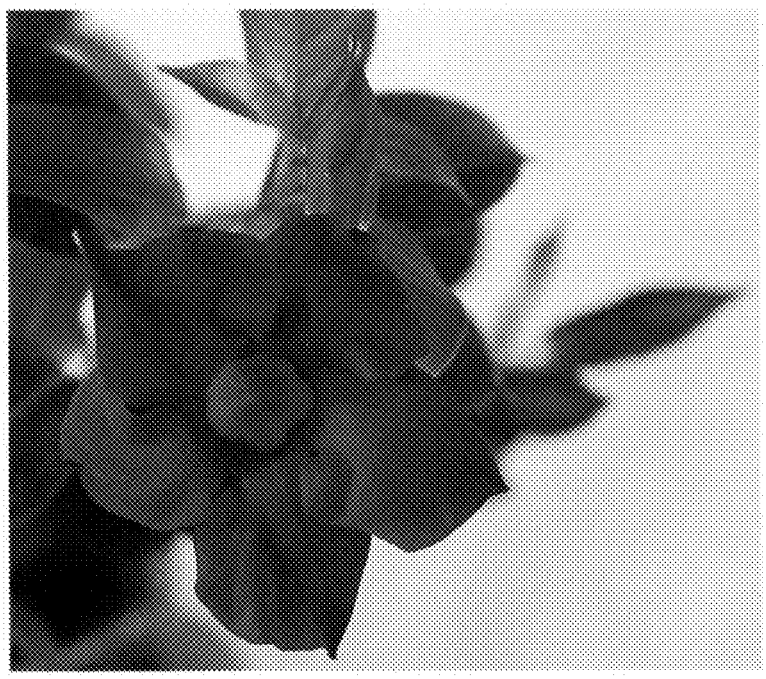
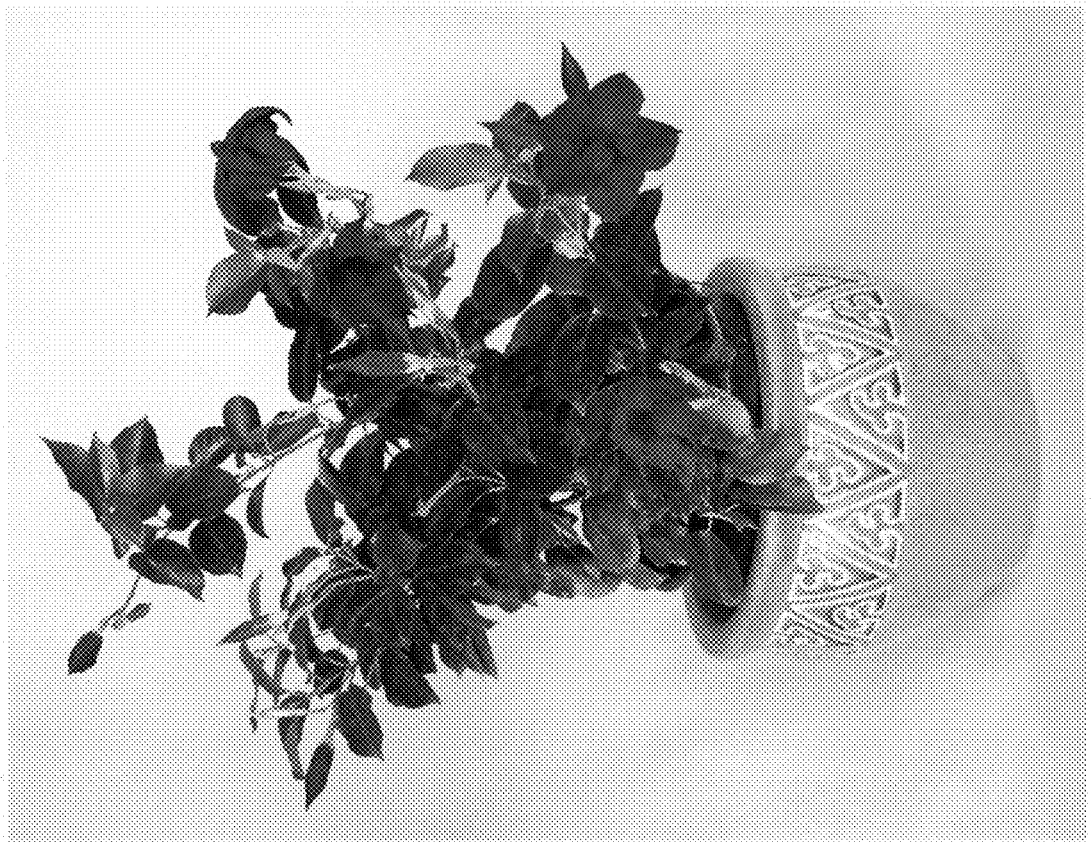

* * * * *